United States Patent
Lacome et al.

(10) Patent No.: US 7,592,470 B2
(45) Date of Patent: Sep. 22, 2009

(54) PROCESS FOR TRANSESTERIFICATION OF VEGETABLE OR ANIMAL OILS USING HETEROGENEOUS CATALYSTS BASED ON TITANIUM, ZIRCONIUM OR ANTIMONY AND ALUMINIUM

(75) Inventors: Thierry Lacome, Condecourt (FR); Gerard Hillion, Herblay (FR); Bruno Delfort, Paris (FR); Renaud Revel, Serpaize (FR); Serge Leporq, Mantes la Ville (FR); Gustave Acakpo, Ris Orangis (FR)

(73) Assignee: Institut Francais du Petrole, Rùeil Malmaison Cedex (FR)

( * ) Notice: Subject to any disclaimer, the term of this patent is extended or adjusted under 35 U.S.C. 154(b) by 1011 days.

(21) Appl. No.: 10/853,725

(22) Filed: May 26, 2004

(65) Prior Publication Data
US 2005/0266139 A1 Dec. 1, 2005

(30) Foreign Application Priority Data

| May 26, 2003 | (FR) | 03 06336 |
| May 26, 2003 | (FR) | 03 06337 |
| May 26, 2003 | (FR) | 03 06338 |

(51) Int. Cl.
*C11C 3/10* (2006.01)
*C09F 7/00* (2006.01)
*C07C 67/02* (2006.01)

(52) U.S. Cl. .......................... 554/169; 554/30; 560/234
(58) Field of Classification Search .............. None
See application file for complete search history.

(56) References Cited

U.S. PATENT DOCUMENTS 5,908,946 A  6/1999 Stern et al.
6,147,196 A  * 11/2000 Stern et al. ............ 554/170
2007/0027338 A1 * 2/2007 Furuta ...................... 560/234

FOREIGN PATENT DOCUMENTS

| FR | 2752242 | 2/1998 |
| GB | 143321 | 5/1920 |
| GB | 712747 | 7/1954 |
| GB | 795573 | 5/1958 |

* cited by examiner

Primary Examiner—Deborah D Carr
(74) Attorney, Agent, or Firm—Millen, White, Zelano, Branigan, P.C.

(57) ABSTRACT

A novel process is described for producing esters of linear monocarboxylic acids containing 6 to 26 carbon atoms, by reacting vegetable or animal oils, neutral or otherwise, with monoalcohols containing 1 to 18 carbon atoms in the presence of a catalyst selected from:
mixtures of titanium oxide and alumina having formula:

$$(TiO_x)_y(Al_2O_3)_{1-y}$$

where x has the value 1.5 to 2.2 and y, representing the weight ratio of the two oxides, has a value of 0.005 to 0.995;
mixtures of zirconium oxide and alumina having formula:

$$(ZrO_x)_y(Al_2O_3)_{1-y}$$

where x has the value 1.5 to 2.2 and y has a value of 0.005 to 0.995;
and mixtures of antimony oxide and alumina having formula:

$$(SbO_x)_y(Al_2O_3)_{1-y}$$

where x has the value 1.2 to 2.6 and y has a value of 0.005 to 0.995, in order to directly produce, in one or more steps, an ester for use as a fuel and a pure glycerin.

20 Claims, No Drawings

PROCESS FOR TRANSESTERIFICATION OF VEGETABLE OR ANIMAL OILS USING HETEROGENEOUS CATALYSTS BASED ON TITANIUM, ZIRCONIUM OR ANTIMONY AND ALUMINIUM

BACKGROUND OF THE INVENTION

1. Field of the Invention

The present invention relates to a novel process for producing esters of monocarboxylic acids from vegetable or animal oils.

The principal reaction is transesterification occurring in accordance with scheme I below, and possibly a coupled esterification and transesterification reaction, esterification occurring in accordance with scheme II below. In these schemes, the fatty acid chains are represented by oleic type chains.

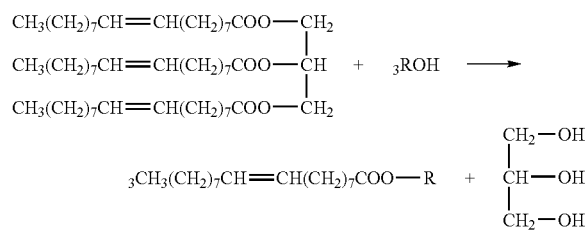

Scheme I

Scheme II

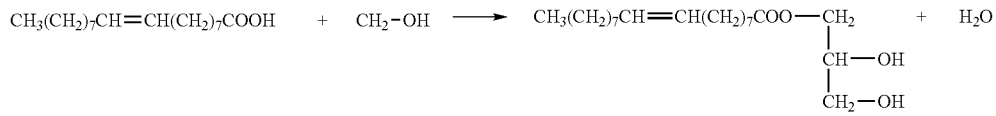

Esters of fatty substances are currently used in a number of applications such as diesel fuel, domestic fuel, solvents, base compounds for the production of sulphonates of fatty alcohols, amides, ester dimers, etc.

When producing an ester from an oil and a monoalcohol, depending on the nature of the starting oil used, 10% to 15% of a secondary product, namely glycerin, is automatically formed. This glycerin fetches a high price and is sold for a variety of uses, but only if it is of high purity. This is achieved after profound purification steps in specialized vacuum distillation units.

When producing methyl esters from fatty substances starting from refined oils and alcohol, although simple alkaline derivatives, such as sodium alcoholates, sodium hydroxide or potassium hydroxide, are currently used as catalysts under fairly mild conditions (temperature of 50° C. to 80° C. and atmospheric pressure), as can be seen from a number of patents or publications such as JAOCS 61, 343-348 (1984), a pure product that can be used as a fuel and a glycerin that satisfy specifications are only produced after a great many steps.

If, for example, the most frequently used catalysts are taken, both the glycerin and the ester contain those alkaline compounds, which must be eliminated by washing and/or neutralization in the ester fraction, then drying. In the glycerin phase, the soaps and alcoholates present must be neutralized, and salts, which are sometimes formed, have to be eliminated.

The glycerin obtained generally contains 5% to 40% by weight of water. It also contains salts from neutralizing the alkaline catalyst, for example sodium chloride when the catalyst is sodium hydroxide or sodium methylate and when neutralization is carried out with hydrochloric acid. The concentration of salts in the glycerin from such processes is generally in the range 3% to 6% by weight. The production of high purity glycerol from glycerin from such processes thus involves purification steps such as reduced pressure distillation, which can sometimes be combined with exchange resin treatments.

In summary, the majority of commercial processes for producing esters can relatively easily produce heavy products (esters and glycerin), which must be purified a great deal using a variety of treatments, which in the end affect the cost of transformation.

It has now, surprisingly, been discovered that it is possible to obtain esters of said monoalcohols and a glycerin that is free of salts, in 1 to 3 steps, under particular conditions, directly from vegetable or animal oils and monoalcohols, and in any case not containing more than 5 ppm, with a purity in the range 95% to 99.9%, usually in the range 98% to 99.9%, by using as the catalyst a particular heterogeneous catalytic system, either continuously, for example in a fixed bed, or discontinuously.

2. Description of the Prior Art

The use of heterogeneous catalysts is not novel.

Examples of prior art documents dealing with heterogeneous catalysts that can be cited include European patent EP-B-0 198 243. The transesterification catalyst, which transforms oil and methanol into the methyl ester, is an alumina or a mixture of alumina and iron oxide. In the examples, the column used for the fixed bed has a volume of 10 liters and in general, oil is injected at a flow rate of less than 1 liter/hour, which produces an HSV (HSV=hourly space velocity=volume of oil injected/volume of catalyst/hour) of less than 0.1. For a factory producing 100,000 tons/yr., this would correspond to reactors of at least 150 m$^3$.

A further problem that appears to arise is that of the quantity of glycerin recovered, which is much lower than theory predicts. None of the examples that claim to collect 10% of glycerin even approaches that value. Finally, the purity of the esters is quite low, 93.5% to 98%. What becomes of the glycerin that is not recovered is not stated. In certain cases, glycerin ethers are formed, as indicated in the patent; in other cases, it may perhaps decompose, unless it is eliminated in a first step. Thus, the performance level is fairly low. It should be indicated that at the indicated HSVs and for a contact time of more than 6 hours, a conversion of 80% and more can be obtained even without a catalyst.

Thus, that patent does not appear to provide a reasonable solution from the point of view of economics.

Other references exist in the literature, this time mentioning zinc oxide, but in reactions for the esterification of glycerin with a fatty acid [Osman in "Fette Seifen und Anstrichmittel", 331-33 (1968)]. In that work, about twenty catalysts are compared at 180° C. in a discontinuous process. There is practically no difference between zinc chloride, zinc sulfate, zinc powder, barium oxide, calcium oxide, zinc oxide, alumina, thiosalicylic acid, calcium phosphate, potassium bicarbonate, sodium methylate or ethylate and even lithium hydroxide. All of the salts or oxides yield between 32% and 39% of monoglyceride in a comparative test in which an excess of glycerin is used with respect to the fatty acid.

U.S. Pat. No. 5,908,946 describes a process which can function continuously or discontinuously using solid non-soluble catalysts. However, the catalysts used are either zinc oxide or a mixture of zinc oxide and alumina, or a zinc aluminate.

SUMMARY OF THE INVENTION

The present invention proposes a process for producing at least one fatty acid ester and glycerin, said two products being obtained with a high level of purity, said process being generally defined in that vegetable or animal oils, which may acidic or neutral, are reacted with monoalcohols containing 1 to 18 carbon atoms, preferably 1 to 12 carbon atoms, for example in the presence of at least one catalyst selected from:

mixtures of titanium oxide and alumina having formula:

$$(TiO_x)_y(Al_2O_3)_{1-y}$$

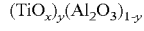

where x has the value 1.5 to 2.2 and y, representing the weight ratio of the two oxides, has a value of 0.005 to 0.995;

mixtures of zirconium oxide and alumina having formula:

$$(ZrO_x)_y(Al_2O_3)_{1-y}$$

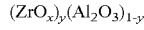

where x has the value 1.5 to 2.2 and y has a value of 0.005 to 0.995;

and mixtures of antimony oxide and alumina having formula:

$$(SbO_x)_y(Al_2O_3)_{1-y}$$

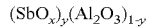

where x has the value 1.2 to 2.6 and y has a value of 0.005 to 0.995.

The conditions for said reaction preferably include a temperature in the range 150° C. to 250° C. and a pressure of less than 100 bar, preferably 10 to 70 bar.

All of the catalysts considered are in the form of powder, beads, extrudates or pellets. Using alumina has two favorable effects.

The first is to increase its specific surface area, as titanium dioxide in its principal crystalline forms (anatase or rutile) and zirconia in its principal crystalline forms (quadratic, monoclinic and cubic) are known to possess low specific surface areas.

The second is to create a much more stable compound, especially under the conditions in which the titanium, zirconium or antimony compound would tend to form titanium, zirconium or antimony soaps.

A further advantage of catalysts based on titanium, zirconium or antimony is their capacity to catalyze transesterification of oil with alcohols that are heavier than methanol. Thus, it is possible to form ethyl esters and also isopropyl or butyl esters, which are of interest outside the fuel field.

A major advantage of these solid catalysts is that they catalyze transesterification and esterification reactions in a heterogeneous catalysis process, i.e. the solid catalyst used is not consumed in the reaction and it is never dissolved in the reaction medium but remains in the solid form and will thus be separated from the liquid reaction medium without loss of catalyst and without polluting the reaction medium by the presence of catalyst or catalyst residue.

This is verified in the invention by the absence of traces deriving from the catalyst both in the ester formed and in the glycerin produced.

The catalyst charge is not affected by the transesterification or esterification reaction. Its catalytic activity is retained after the reaction. This type of catalyst is compatible with use in a continuous industrial process, for example in a fixed bed process in which the catalyst charge can be used over a very long period with no loss of activity.

The ester and glycerol obtained contain no impurities derived from the catalyst. Because of this fact, no purification treatment needs to be applied to eliminate the catalyst or its residues, in contrast to processes using homogeneous catalysts where the catalyst or its residue is located in the same phase as the ester and/or the glycerin following reaction.

By carrying out said process, final purification is reduced to a minimum, while obtaining an ester that satisfies fuel specifications, and a glycerin with a purity in the range 95% to 99.9%, preferably in the range 98% to 99.99%.

DETAILED DESCRIPTION OF THE INVENTION

The process of the invention will be described in more detail below.

Oils used in the process of the invention that can be cited include all current oils such as African, palm nut, copra, babassu, old or fresh rapeseed, sunflower, corn, castor or cottonseed oil, peanut oil, linseed oil and crambe oil and all oils derived from sunflower or rape by genetic modification or hybridization, for example.

It is also possible to use frying oils, various animal oils such as fish oils, tallow, suet, rendering oil and even fats.

Useful oils also include oils that are partially modified, for example by polymerization or oligomerization, such as stand oil, linseed oil, sunflower seed oil and blown vegetable oils.

A priori, the presence of fatty acid in the oils is not prejudicial, apart from a risk of saponification. It is possible to precede the transesterification reaction by an esterification reaction, preferably with glycerin, to form a glyceride from the fatty acids at atmospheric pressure or under partial vacuum, and at temperatures of 180° C. to 220° C.

The nature of the alcohol used in the process of the invention plays an important role in transesterification activity. In general, a variety of aliphatic monoalcohols containing, for example, 1 to 18 carbon atoms, preferably 1 to 12 carbon atoms, can be used. The most active is methyl alcohol. However, ethyl alcohol and isopropyl, propyl, butyl, isobutyl and even amyl alcohol can be used. It is also possible to use heavier alcohols such as ethylhexyl alcohol or lauryl alcohol. Advantageously, methyl alcohol can be added to the heavy alcohols, which appears to facilitate the reaction. Further, when preparing the ethyl ester, it is possible to use 1% to 50%, preferably 1% to 10%, of methyl alcohol to increase conversion.

The preparation of titanium based catalysts is not novel. U.S. Pat. No. 4,490,479, for example, concerns the synthesis of the catalyst by co-mixing. In particular, the authors describe the addition of oxides, hydroxides, alkoxides or salts of titanium to a precursor of alumina or hydrated aluminum compounds. In the presence of water and mineral or organic acids, the above elements mix to form a paste. The latter is shaped to obtain a support. A second step describes adding a molybdenum compound.

U.S. Pat. No. 5,169,822 discloses the deposition of titanium alkoxides on inorganic supports (inter alia) in non-aqueous media.

The article by S. Kumar et al in Mat. Lett. 43 (2000) 286 discloses the precipitation of a boehmite sol with a titanium dioxide sol. The titanium sol is prepared by stabilization with acetic acid.

To produce a catalyst with basic formula $(TiO_x)_y(Al_2O_3)_{1-y}$ (x and y being as defined above), the following sources can be used.

Sources of titanium that can be cited include alkoxide forms $Ti(OR)_4$ in which R=Me, Et, Pr, iPr, Bu, iBu, etc. It is also possible to use titanium in the form of inorganic salts ($TiCl_4$, $TiOSO_4$, $TiOCl_2$, etc). Similarly, colloidal forms of titanium can be used (the term "colloidal" as used by the Applicant means that the particle size of the titanium oxide or oxyhydroxide is in the range 1 nm to 100 nm). Finally, the titanium sources can be gels from hydrolysis of the above sources, producing a partially hydrated form of titanium oxide with chemical formula ($TiO_2$, $zH_2O$) in which z is in the range 0 to 5. It is also advantageous to use dehydrated titanium oxide, amorphous or crystalline, which in the latter case has quadratic, monoclinic or cubic crystallographic structures, which are known to the skilled person.

The preparation of zirconium based catalysts is known in the art. A particular method deriving from the disclosure of EP-B-0 908 232 consists of co-precipitating $ZrO(NO_3)_2$ and $Al(NO_3)_3$ at a pH of 9.

A further method inspired by the work of Gao et al (Top Catal. 6 (1998), 101) consists of co-precipitating $ZrOCl_2$ and $Al(NO_3)_3$ with ammonia.

A preferred method is the precipitation of $ZrO(NO_3)_2$ with hydrazine in the presence or absence of $Al(NO_3)_3$ (for example, the method cited by Ciuparu et al, J. Mater. Sci. Lett. 19 (2000) 931).

To produce a catalyst with basic formula $(ZrO_x)_y(Al_2O_3)_{1-y}$ (x and y being as defined above), it is possible to use the following sources.

Sources of zirconium that can be cited include alkoxide forms $Zr(OR)_4$ in which R=Me, Et, Pr, iPr, Bu, iBu, etc). It is also possible to use zirconium in the form of inorganic salts ($ZrOCl_2$, $ZrOSO_4$, $ZrO(NO_3)_2$, etc). Similarly, colloidal forms of zirconium can be used (the term "colloidal" as used by the Applicant means that the particle size of the zirconium oxide or oxyhydroxide is in the range 1 nm to 100 nm). Finally, the zirconium sources can be gels from hydrolysis of the above sources, producing a partially hydrated form of zirconium oxide with chemical formula ($ZrO_2$, $zH_2O$) in which z is in the range 0 to 5. It is also advantageous to use dehydrated zirconium oxide, amorphous or crystalline, which in the latter case has quadratic, monoclinic or cubic crystallographic structures, which are known to the skilled person.

To produce a catalyst with basic formula $(SbO_x)_y(Al_2O_3)_{1-y}$ (x and y being as defined above), it is possible to use the following sources.

Sources of antimony that can be cited include alkoxide forms $Sb(OR)_4$ in which R=Me, Et, Pr, iPr, Bu, iBu, etc. It is also possible to use antimony in the form of inorganic salts ($SbCl_3$, $SbCl_5$, $Sb(acac)_3$, $SbF_3$, $SbF_5$, etc). Similarly, colloidal forms of antimony can be used (the term "colloidal" as used by the Applicant means that the particle size of the antimony oxide or oxyhydroxide is in the range 100 nm to 150 μm). Finally, the antimony sources can be gels from hydrolysis of the above sources, obtaining a partially hydrated form of antimony oxide with chemical formula ($SbO_2$, $zH_2O$) in which y is in the range 1.2 to 2.6 and z is in the range 0 to 5. It is also advantageous to use oxides of antimony ($Sb_2O_3$, $Sb_2O_4$, and Sb2O5), dehydrated to a greater or lesser extent, amorphous or crystalline, which in the latter case has crystallographic structures, which are known to the skilled person.

Sources of Alumina

The sources of aluminum used in the invention can be in the alkoxide form with general formula $Al(OR)_3$, in which R=Me, Et, Pr, iPr, Bu, iBu, etc or hydroxides. Inorganic aluminum salts can also advantageously be used, namely chlorides, nitrates, sulfates, etc. Similarly, the aluminum source can be basic, in which case the aluminum is in the form of the aluminate ($AlO_2^-$). The counter-ion can be an alkali (Li, Na, K, Cs) and more generally any positive counter-ion ($NH_4^+$, for example). When a solid aluminum precursor is used, any alumina compound with general formula $Al_2O_3$, $nH_2O$ can be used. Its specific surface area is in the range 100 to 600 $m^2/g$. In particular, it is possible to use hydrated compounds of alumina such as hydrargillite, gibbsite, bayerite, boehmite, pseudo-boehmite and amorphous or essentially amorphous alumina gels. It is also possible to use dehydrated forms of said compounds, which are constituted by transition aluminas and which comprise at least one phase taken from the group: rho, khi, eta, kappa, theta, delta, gamma and alpha, which differ essentially in the organization of their crystalline structure.

The catalyst can advantageously be prepared using one of the methods described below.

Impregnation of at least one soluble salt, an alkoxide, a sol or an alkoxide onto a preformed alumina support with a specific surface area in the range 20 to 600 $m^2/g$, preferably in the range 100 to 370 $m^2/g$. This support can be in the form of powder, beads, extrudates or any other form known to the skilled person and which can be employed in a fixed bed, ebullated bed or slurry configuration. This support is selected from the alumina sources cited above. After a variety of steps that are known to the skilled person, the catalysts are dried between 25° C. and 150° C., preferably between 50° C. and 120° C., then calcined at temperatures in the range 150° C. to 1,000° C., preferably between 250° C. and 600° C.

Mixing at least one titanium, zirconium or antimony compound with an alumina compound that is hydrated to a greater or lesser extent as defined above as a solid precursor in the presence of a peptizing agent (mineral or organic acid). Preferably, the peptizing agents are nitric and acetic acids. The paste obtained can also be supplemented with agents that are known to facilitate forming, such as methyl cellulose type derivatives or any other compound that is known to the skilled person for this purpose. The product is then formed by extrusion, dried between 40° C. and 150° C., preferably between 70° C.

and 120° C., and calcined at temperatures in the range 300° C. to 1100° C., preferably in the range 350° C. and 800° C.

Sol-gel type synthesis between a titanium, zirconium or antimony alkoxide and an aluminum alkoxide, selected from the sources cited above, preferably aluminum sec-butoxide, titanium butoxide or isopropoxide, zirconium n-butoxide or antimony butoxide. These precursors can be mixed in the presence of a suitable solvent and possibly a complexing agent or surfactants. The ensemble can be hydrolyzed to obtain a gel. The gel can be dried between 40° C. and 140° C., preferably between 80° C. and 130° C. and formed using conventional extrusion techniques, possibly with the addition of a binder, or by taking up into suspension in a suitable liquid to form beads by oil drop precipitation, or palletized. In all cases, the articles that are formed are dried between 40° C. and 150° C., preferably between 70° C. and 120° C., then calcined at temperatures in the range 300° C. to 1100° C., preferably between 350° C. and 800° C.

Co-precipitation between at least one titanium, zirconium or antimony salt, a titanium, zirconium or antimony sol or alkoxide and at least one aluminum salt, sol or alkoxide in an aqueous pathway. Co-precipitation can take place in the presence of water alone or of agents encouraging precipitation, such as an inorganic base (sodium hydroxide, potassium hydroxide, sodium carbonate, ammonia, hydrazine, etc) or an organic base (urea etc), or an inorganic acid (nitric acid, sulfuric acid, etc) or an organic acid (formic acid, acetic acid etc). Precipitation must take place at a pH of between 4 and 13, as is known to the skilled person, more preferably between 5 and 9. The co-precipitate is filtered and washed carefully as a function of the nature of the precursors and it agents so as to limit the alkali ion contents (sodium, potassium, etc) to less than 0.5% and preferably to less than 0.1% by weight with respect to the oxides. Similarly, the anion contents (chloride, sulfate, etc) must be limited to less than 1%, preferably to less than 0.3% by weight. The precipitate obtained can be spray dried then formed by extrusion, pelletization or taking up in suspension in a suitable solvent to form beads. In all cases, the shaped articles are dried between 40° C. and 150° C., preferably between 70° C. and 120° C., then calcined at temperatures in the range 300° C. to 1100° C., preferably in the range 350° C. to 800° C.

Whatever the preparation method used, it is preferable to use at least 10% of titanium, zirconium or antimony oxide, preferably 23% of titanium, zirconium or antimony oxide and more preferably 50% of titanium, zirconium or antimony oxide. As far as possible, the titanium, zirconium or antimony oxides must be primarily in the amorphous or micro-crystalline form, indicated by the absence of peaks in the X ray diffraction diagram relating to crystalline forms of titanium, zirconium or antimony oxide, which are known to the skilled person.

Regarding the texture of the catalyst, it is important to maintain the specific surface area measured by the BET method, which is known to the skilled person, and the pore volume must be kept to the correct values. The catalyst will generally have a specific surface area in the range 10 to 500 $m^2/g$, preferably in the range 50 to 400 $m^2/g$ and more preferably in the range 80 to 300 $m^2/g$. Similarly, the pore volume is in the range 0.1 $cm^3/g$ to 1.2 $cm^3/g$, preferably more than 0.2 $cm^3/g$. Finally, the pore distribution is in the range 0.001 microns to 0.1 microns.

If transesterification is carried out in the absence of a catalyst either in an autoclave or in a fixed bed with inert supports such as silicon carbide, at certain temperatures generally of 250° C. or more, it is possible to obtain conversions that exceed 80% are obtained but at very low HSVs and with very long residence times. Thus, the thermal reaction exists and it is sometimes difficult to distinguish between the catalytic effect and the thermal effect, which can be explained by the fact that with simple aluminas, it is possible to obtain high conversions. However, the aim of the process of the invention is to obtain these conversions in reasonable residence times and thus at reasonable HSVs.

The operating conditions employed depend substantially on the selected process. if a discontinuous reaction is used, one or two steps can be employed, i.e. a first reaction up to 85% to 95% conversion, with cooling and evaporating off the excess methanol, decanting the glycerin and finishing the reaction by reheating and adding alcohol to obtain complete conversion. It is also possible to envisage a conversion of 98% by operating for a sufficient period in a single step. Furthermore, an aspect of the invention is to provide the following successive steps:

initial transesterification with an oil to ester conversion of at least 80-85%;

evaporating off the excess monoalcohol;

decanting the glycerin and the ester, said ester being recycled to a second step to undergo transesterification with a portion of the monoalcohol recovered in the first evaporation;

then evaporating off the monoalcohol once more, cold decanting and separating the glycerin from the ester.

If a continuous reaction is employed, a plurality of autoclaves and decanters can be used. In the first, a conversion of 85% is achieved, for example, then decantation with evaporation of the alcohol and cooling is carried out; in a second reactor, the transesterification reaction is completed by adding a portion of the alcohol that had previously been evaporated off. Finally, the excess alcohol is evaporated off in an evaporator and the glycerin and esters are separated by decanting.

If a continuous fixed bed process is selected, it is advantageous to operate at temperatures of 150° C. to 250° C., preferably 170° C. to 210° C., at pressures of 30 to 70 bar, if methyl esters are produced, the HSV preferably being in the range 0.1 to 3, more preferably 0.3 to 2 in the first step and the weight ratio of the alcohol/oil being from 3/1 to 0.1/1.

The alcohol can advantageously be introduced in a fractionated manner. Introduction into the tube reactor at two levels can be carried out as follows: supplying the reactor with oil and about ⅔ of the alcohol to be employed, then introducing the complement of the alcohol into approximately the upper third of the catalytic bed.

If 220° C. are not exceeded then generally an ester with the same color as the starting oil and a colorless glycerin are obtained after decanting. The ester can be passed over a resin, earth and/or activated charcoal, as can the glycerin.

The compounds produced are analyzed either by gas chromatography for the esters and the glycerin or, more rapidly, by liquid exclusion chromatography for the esters. It is shown that the process of the invention, in contrast to known processes carried out using homogeneous basic catalysis with monoalcohols, produces few or no sterol esters. Sterol esters, which are heavy products, can cause deposits in the injectors.

The entire disclosure of all applications, patents and publications, cited above and below, and of French applications 03/06336, 03/06337 and 03/06338, filed May 26, 2003, the priority of which is claimed, are hereby incorporated by reference.

The following examples do not limit the invention and are presented solely by way of illustration.

Catalyst Synthesis

Catalyst 1.1

A preformed alumina support in the form of 1.4-mm diameter beads was used, with a specific surface area $S_{BET}$ of 189 $m^2/g$ and with a pore volume $V_p$ of 0.6 $cm^3/g$.

Catalyst 1.2

Catalyst 1.2 was prepared in accordance with S. Kumar et al, Mat. Lett. 43 (2000), 286. 336 g of titanium isopropoxide was introduced into a reactor. 600 ml of acetic acid was added to the titanium solution and the ensemble was mixed for 30 minutes. 1800 ml of water was slowly added to this solution, with constant stirring. 708 g of boehmite sol, 10% by weight, was added to this solution. Stirring was maintained for 30 minutes. The mixture was placed under autogenous pressure at 100° C. to produce a gel. The gel obtained was filtered, dried then spray dried. The powder obtained was formed by extrusion. The extrudates were then calcined at 600° C. for 3 h. X-ray diffraction analysis showed the presence of a crystalline phase, characteristic of the presence of gamma alumina. No characteristic lines for rutile or anatase phases were detected. The specific surface area, measured using the BET method, was 145 $m^2/g$. The alumina and titanium dioxide contents, measured by X ray fluorescence, were 51% and 49% by weight respectively.

Catalyst 1.3

Catalyst 1.3 was prepared by impregnating titanium butoxide into catalyst 1.1. The alumina was calcined at 400° C. for 1 h. 55.45 g of titanium butoxide was mixed with 5 ml of heptane, then slowly poured onto 87 g of alumina. The ensemble was stirred for 24 h. The solid obtained was placed in ambient air for 72 h, then oven dried. The catalyst was calcined at 500° C. for 4 h. X-ray diffraction analysis showed the presence of a crystalline phase, characteristic of the presence of gamma alumina. No lines that were characteristic of rutile or anatase phases were detected. The specific surface area, measured using the BET method, was 185 $m^2/g$. The alumina and titanium dioxide contents, measured by X ray fluorescence, were 87.5% and 12.5% by weight respectively.

Catalyst 1.4

Catalyst 1.4 was prepared as described in U.S. Pat. No. 4,490,479. 91 g of boehmite (Pural SB3) was mixed with 39 g of titanium gel (Gel G5 Millenium) in the presence of 3.2 g of 70% nitric acid and 122 g of water. The components were mixed for 1 h to form a paste. The paste obtained was converted into 1.6-mm diameter extrudates, which were dried at 120° C. for 20 h and calcined in air at 450° C. for 10 h. X-ray diffraction analysis showed the presence of a crystalline phase, characteristic of the presence of gamma alumina. No lines that were characteristic of rutile or anatase phases were detected. The specific surface area, measured using the BET method, was 163 $m^2/g$. The alumina and titanium dioxide contents, measured by X ray fluorescence, were 70.5% and 29.5% by weight respectively.

Catalyst 1.5

A titanium support SCS41 was used. Its specific surface area was 98 $m^2/g$.

Catalyst 1.6

Catalyst 1.6 was prepared as described in U.S. Pat. No. 4,490,479. 95 g of boehmite (Pural SB3) was mixed with 30 g of titanium dioxide in the presence of 7 g of 70% nitric acid and 110 g of water. The components were mixed for 1 h to form a paste. The paste obtained was converted into 1.4-mm diameter extrudates, which were dried at 120° C. for 20 h and calcined in air at 550° C. for 10 h. X-ray diffraction analysis showed the presence of crystalline phases, characteristic of the presence of gamma alumina and anatase. The specific surface area, measured using the BET method, was 136 $m^2/g$. The alumina and titanium dioxide contents, measured by X ray fluorescence, were 69.2% and 31.8% by weight respectively.

Catalyst 2.2

Catalyst 2.2 was prepared in accordance with Ciuparu (J. Mater. Sci. Lett. 19 (2000) 931). Zirconyl nitrate was mixed with hydrazine, and the ensemble was placed under reflux for 120 h. The gel obtained was filtered, dried then spray dried. The powder obtained was formed by extrusion. The extrudates were calcined at 550° C. for 4 h. X ray diffraction analysis showed that the zirconia was amorphous, as no peaks characteristic of the presence of known crystallographic phases of zirconia were detected. The specific surface area, measured using the BET method, was 250 $m^2/g$. The zirconia content was 100%.

Catalyst 2.3

Catalyst 2.3 was prepared by impregnating zirconium n-butoxide into catalyst 1.1. The alumina was calcined at 400° C. for 1 h. 92.7 g of zirconium n-butoxide was mixed with 64 ml of heptane, then slowly poured onto 100 g of alumina. The ensemble was stirred for 24 h. The solid obtained was placed in ambient air for 72 h, then oven dried. The catalyst was calcined at 500° C. for 4 h. X-ray diffraction analysis showed the presence of a crystalline phase, characteristic of the presence of gamma alumina. Further, a small proportion of tetragonal zirconia was detected. The specific surface area, measured using the BET method, was 193 $m^2/g$. The alumina and zirconia contents, measured by X ray fluorescence, were 84.3% and 14.7% by weight respectively.

Catalyst 2.4

Catalyst 2.4 was prepared by co-precipitating zirconyl nitrate and aluminum sulfate to which ammonium had been added. The gel obtained was filtered, dried then spray dried. The powder obtained was formed by extrusion. The extrudates were then calcined at 700° C. for 4 h. X-ray diffraction analysis indicated the presence of amorphous zirconia; no characteristic peaks for known crystallographic phases of zirconia were detected. The specific surface area, measured using the BET method, was 158 $m^2/g$. The alumina and zirconia contents were 15% and 85% by weight respectively.

Catalyst 3.2

Catalyst 3.2 was prepared in accordance with EP-B-0 197 503. 216 g of aluminum chloride $AlCl_3, 6H_2O$ (Aldrich) previously mixed with 357 ml of water and brought to a pH of 3.4 was added to 143 g of 38% Nyacol A1540N antimony sol. Addition was accompanied by vigorous stirring and mixing was maintained for 3 h. A white colloidal solution appeared. The pH of said solution was then increased by adding 15.3 g of 28% ammonia. After maturing for two hours, the ensemble was filtered, washed with water then dried. The powder obtained was formed by extrusion. The extrudates were calcined at 550° C. for 4 h. The specific surface area, measured using the BET method, was 102 m²/g. The antimony oxide content was 54%.

Catalyst 3.3

Catalyst 3.3 was prepared by impregnating antimony butoxide into catalyst 1.1. 61.4 g of antimony butoxide was mixed with 52 ml of heptane, then slowly poured onto 82 g of alumina. The ensemble was stirred for 24 h. The solid obtained was placed in ambient air for 72 h, then oven dried. The catalyst was calcined at 350° C. for 4 h. X-ray diffraction analysis showed the presence of a crystalline phase, characteristic of the presence of gamma alumina. The specific surface area, measured using the BET method, was 155 m²/g. The antimony content, measured by X-ray fluorescence, was 13.8%.

Catalyst 3.4

Catalyst 3.4 was prepared by impregnating antimony butoxide into catalyst 1.1. 163.4 g of antimony butoxide was mixed with 90 ml of hexane, then slowly poured onto 150 g of alumina. The ensemble was stirred for 24 h. The solid obtained was placed in ambient air for 72 h, then oven dried. The catalyst was calcined at 350° C. for 4 h. X-ray diffraction analysis showed the presence of a crystalline phase, characteristic of the presence of gamma alumina. The specific surface area, measured using the BET method, was 128 m²/g. The antimony content, measured by X-ray fluorescence, was 29.3%.

Catalyst 3.5

Catalyst 3.5 was prepared by introducing 86.4 g of alumina gel into a mixer in the presence of 85 ml of an aqueous solution containing 4.5 g of 68% nitric acid. After mixing for 20 minutes, 96 g of $Sb_2O_3$ and 20 ml of water were added. After mixing for 20 minutes, the paste obtained was flexible and could readily be extruded. Extrusion was carried out in an extruder equipped with a 1.4-mm diameter die. The extrudates obtained were dried in a ventilated oven for 4 h at 100° C. then for 3 h at 150° C. Calcining was carried out in a muffle furnace for 3 h at 350° C. and/or 2 h at 500° C., programming the temperature rise to 6° C./min. The specific surface area, measured using the BET method, was 105 m²/g. The antimony content, measured by X-ray fluorescence, was 41%.

EXAMPLE 1 (COMPARATIVE)

Reaction in the Absence of Catalyst 25 g of rapeseed oil the composition of which is shown in the table below and 25 g of methanol were introduced into a 100-ml autoclave reactor provided with a stirring system and a temperature and pressure regulator.

| Fatty acid glyceride | nature of fatty chain | % by weight |
| --- | --- | --- |
| palmitic | C16:0 | 5 |
| palmitoleic | C16:1 | <0.5 |
| stearic | C18:0 | 2 |
| oleic | C18:1 | 59 |
| linoleic | C18:2 | 21 |
| linolenic | C18:3 | 9 |
| arachidic | C20:0 | <0.5 |
| gadoleic | C20:1 | 1 |
| behenic | C22:0 | <0.5 |
| erucic | C22:1 | <1 |

The medium was heated to 200° C. with stirring. The pressure reached 32 bars.

Samples were taken after 2 hours, 5 hours and 7 hours. For each sample, after filtering then evaporating off the excess methanol and eliminating the glycerol formed by decanting, the concentration of methyl esters was determined by steric exclusion chromatography. It was 18%, 36% and 52% respectively.

EXAMPLE 2 (COMPARATIVE)

Reaction in the Presence of Catalyst 1.1

25 g of rapeseed oil the composition of which was shown in Example 1, 25 g of methanol and 5 g of catalyst 1.1 were introduced into a 100 ml autoclave reactor provided with a stirring system and a temperature and pressure regulator. The medium was heated to 200° C. with stirring. The pressure reached 32 bars.

Samples were taken after 2 hours, 5 hours and 7 hours. For each sample, after filtering then evaporating off the excess methanol and eliminating the glycerol formed by decanting, the concentration of methyl esters was determined by steric exclusion chromatography. It was 18%, 35% and 54% respectively. These results are similar to those reported in Example 1 in the absence of a catalyst, indicating that the product termed catalyst 1.1 constituted solely by alumina had no catalytic effect under the experimental conditions.

EXAMPLE 3

25 g of rapeseed oil the composition of which was shown in Example 1, 25 g of methanol and 5 g of catalyst 1.3 were introduced into a 100 ml autoclave reactor provided with a stirring system and a temperature and pressure regulator. The medium was heated to 200° C. with stirring. The pressure reached 32 bars.

Samples were taken after 2 hours, 5 hours and 7 hours. For each sample, after filtering then evaporating off the excess methanol and eliminating the glycerol formed by decanting, the concentration of methyl esters was determined by steric exclusion chromatography. It was 68%, 89% and 95% respectively.

The titanium concentration in the methyl ester obtained was less than 1 ppm, which confirmed the heterogeneous character of the catalysis.

This allowed the ester obtained to be used as a fuel without having to carry out an additional treatment for purifying the methyl ester to eliminate traces of residual catalyst.

Under the same conditions, the same recycled catalyst produced a methyl ester concentration of 95% after 7 hours of reaction, which indicated that the catalyst had not degraded at all and that it had conserved its activity. This operation was repeated twice more and led to the same conclusions.

EXAMPLE 4

Example 3 was repeated, using 5 g of catalyst 1.6.

Samples were taken after 2 hours, 5 hours and 7 hours. For each sample, after filtering then evaporating off the excess methanol and eliminating the glycerol formed by decanting, the concentration of methyl esters was determined by steric exclusion chromatography. It was 67%, 87% and 94% respectively.

The titanium concentration in the methyl ester obtained was less than 1 ppm, which confirmed the heterogeneous character of the catalysis.

EXAMPLES 7 TO 9

Methanolysis was carried out in an apparatus comprising a fixed bed reactor, i.e. a filled column with a diameter of 1.9 cm and a length of 120 cm, heated using 3 sheaths surrounding the column. The oil and methanol were preheated in the column on 10 cm³ of glass beads and the reaction was carried out on 70 cm³ of catalyst 1.3. At the column outlet, 20 cm³ of tungsten carbide and 5 cm³ of glass beads were added. The upturned U device was constituted by a tube reactor, a cooler over the horizontal portion and a decanter, which constituted the second branch. Over the upper portion of the decanter, a gas purge system enabled the pressure to be regulated, i.e., to be maintained from start-up with nitrogen at the desired pressure of 15 to 60 bars. The decanter had a liquid purge at its lower outlet. When the decanter was half full, an automatic valve opens to partially evacuate the product obtained. Two pumps inject the alcohol and oil from bottom to top into the column at the desired flow rate and constant pressure.

The reaction products were recovered after 24 hours passage at the desired HSVs (HSV=volume of oil/volume of catalyst/hour).

After extracting the product constituted by methanol, glycerol and ester, generally present in a single phase, the methanol was evaporated, and then the ester and glycerol were separated by decanting.

The ester was analyzed by steric exclusion chromatography. The results were thus those obtained without any final purification, apart from evaporating off the excess methanol and separating the ester from the glycerin by decanting, preferably at about 50° C.

The table below shows the results obtained after 24 hours of reaction.

The HSV is the volume of oil injected per volume of catalyst per hour. The ratio R is the ratio of oil/alcohol by volume, O/A. The pressure is the pressure reigning in the decanter, expressed in bars.

The composition of the mixture is expressed as a % by weight.

The contact time took into account the presence of methanol; it was determined by the relationship:

$$\text{Contact time} = \frac{70 \text{ cm}^3 \text{ of catalyst} \times 60(*)}{\text{volume in cm}^3 \text{ of oil} + \text{alcohol injected in 1 h}}$$

(*) 60 = time in minutes

In the table:
E=esters (also containing sterols);
MG=monoglycerides;
DG=diglycerides, which contain no sterol esters, as they are not formed under these conditions;
TG=triglycerides.

Methanolysis of Rapeseed Oil with Catalyst 1.3

| Ex. | T (° C.) | HSV | O/A ratio vol./vol. | P (bar) | TG (%) | DG (%) | MG (%) | E (%) | contact time (min) |
|---|---|---|---|---|---|---|---|---|---|
| 7 | 200 | 0.5 | 1 | 50 | 0.6 | 1.5 | 2.9 | 95.0 | 60 |
| 8 | 200 | 0.5 | 1.5 | 50 | 4.2 | 2.8 | 3.7 | 89.3 | 72 |
| 9 | 180 | 0.5 | 1 | 50 | 3.0 | 5.4 | 7.8 | 83.8 | 60 |

Titanium X ray fluorescence analysis was carried out on the methyl esters and the glycerol obtained. The absence of titanium in these products confirmed the heterogeneous nature of the catalyst.

EXAMPLE 10

Example 7 was repeated, replacing rapeseed oil used as the charge with an ester mixture the composition of which was identical to that obtained in Example 7.

The composition of the ester phase obtained was:

| | |
|---|---|
| Methyl esters: | 99.5% |
| Monoglycerides: | 0.4% |
| Diglycerides: | 0.1% |
| Triglycerides: | not detected |

This composition was compatible with the required specifications for a diesel engine fuel ester.

EXAMPLE 11

25 g of rapeseed oil the composition of which was shown in Example 1, 25 g of methanol and 5 g of catalyst 3 were introduced into a 100 ml autoclave reactor provided with a stirring system and a temperature and pressure regulator. The medium was heated to 200° C. with stirring. The pressure reached 32 bars.

Samples were taken after 2 hours, 5 hours and 7 hours. For each sample, after filtering then evaporating off the excess methanol and eliminating the glycerol formed by decanting, the concentration of methyl esters was determined by steric exclusion chromatography. It was 58%, 83% and 90% respectively.

The zirconium concentration in the methyl ester obtained was less than 1 ppm, which confirmed the heterogeneous character of the catalysis.

This allowed the ester obtained to be used as a fuel without having to carry out an additional treatment for purifying the methyl ester to eliminate traces of residual catalyst.

Under the same conditions, the same recycled catalyst produced a methyl ester concentration of 90% after 7 hours of reaction, which indicated that the catalyst had not degraded at all and that it had conserved its activity. This operation was repeated twice more and led to the same conclusions.

EXAMPLE 12

Example 11 was repeated, this time using 16.7 g of methanol instead of 2 g. Samples were taken after 2 hours, 5 hours and 7 hours. For each sample, after filtering then evaporating off the excess methanol and eliminating the glycerol formed by decanting, the concentration of methyl esters was determined by steric exclusion chromatography. It was 53%, 68% and 83% respectively.

The zirconium concentration in the methyl ester obtained was less than 1 ppm, which confirmed the heterogeneous character of the catalysis.

Under the same conditions, the same recycled catalyst produced a methyl ester concentration of 83% after 7 hours of reaction, which indicated that the catalyst had not degraded at all and that it had conserved its activity.

EXAMPLE 13

Example 11 was repeated, this time operating at 180° C. instead of 200° C. The pressure reached 27 bars.

Samples were taken after 2 hours, 5 hours and 7 hours. For each sample, after filtering then evaporating off the excess methanol and eliminating the glycerol formed by decanting, the concentration of methyl esters was determined by steric exclusion chromatography. It was 38%, 58% and 65% respectively.

The zirconium concentration in the methyl ester obtained was less than 1 ppm, which confirmed the heterogeneous character of the catalysis.

Under the same conditions, the same recycled catalyst produced a methyl ester concentration of 65% after 7 hours of reaction, which indicated that the catalyst had not degraded at all and that it had conserved its activity.

EXAMPLES 14 TO 16

The procedure of Examples 7 to 9 was carried out, using 70 cm$^3$ of catalyst 2.3.

The table below shows the results obtained after 24 hours of reaction.

In the table:
E=esters (also containing sterols);
MG=monoglycerides;
DG=diglycerides, which contain no sterol esters, as they are not formed under those conditions;
TG=triglycerides.

Methanolysis of Rapeseed Oil with Catalyst 2.3

| Ex. | T (° C.) | HSV | O/A ratio vol./vol. | P (bar) | TG (%) | DG (%) | MG (%) | E (%) | contact time (min) |
|---|---|---|---|---|---|---|---|---|---|
| 14 | 200 | 0.5 | 1 | 50 | 0.6 | 1.9 | 3.5 | 94.0 | 60 |
| 15 | 200 | 0.5 | 1.5 | 50 | 4.3 | 3.9 | 4.6 | 87.2 | 72 |
| 16 | 180 | 0.5 | 1 | 50 | 5.2 | 5.4 | 7.9 | 81.5 | 60 |

Zirconium X ray fluorescence analysis was carried out on the methyl esters and the glycerol obtained. The absence of zirconium in these products confirmed the heterogeneous nature of the catalyst.

EXAMPLE 17

The procedure of Example 14 was followed, replacing the rapeseed oil used as the feed with an ester mixture the composition of which was identical to that obtained in Example 14.

The composition of the ester phase obtained was:

| | |
|---|---|
| Methyl esters: | 99.3% |
| Monoglycerides: | 0.5% |
| Diglycerides: | 0.2% |
| Triglycerides: | not detected |

This composition was compatible with the required specifications for a diesel engine fuel ester.

EXAMPLE 18

25 g of rapeseed oil the composition of which was shown in Example 1, 25 g of methanol and 5 g of catalyst 3.3 were introduced into a 100 ml autoclave reactor provided with a stirring system and a temperature and pressure regulator. The medium was heated to 200° C. with stirring. The pressure reached 32 bars.

Samples were taken after 2 hours, 5 hours and 7 hours. For each sample, after filtering then evaporating off the excess methanol and eliminating the glycerol formed by decanting, the concentration of methyl esters was determined by steric exclusion chromatography. It was 86%, 96% and 96% respectively.

The antimony concentration in the methyl ester obtained was less than 2 ppm, which confirmed the heterogeneous character of the catalysis.

This allowed the ester obtained to be used as a fuel without having to carry out an additional treatment for purifying the methyl ester to eliminate traces of residual catalyst.

Under the same conditions, the same recycled catalyst produced a methyl ester concentration of 96% after 7 hours of reaction, which indicated that the catalyst had not degraded at all and that it had conserved its activity. This operation was repeated twice more aid led to the same conclusions.

EXAMPLE 19

Example 18 was repeated, this time using 5 g of catalyst 3.5.

Samples were taken after 2 hours, 5 hours and 7 hours. For each sample, after filtering then evaporating off the excess methanol and eliminating the glycerol formed by decanting, the concentration of methyl esters was determined by steric exclusion chromatography. It was 67%, 87% and 94% respectively.

The antimony concentration in the methyl ester obtained was less than 1 ppm, which confirmed the heterogeneous character of the catalysis.

Under the same conditions, the same recycled catalyst produced a methyl ester concentration of 93% after 7 hours of reaction, which indicated that the catalyst had not degraded at all and that it had conserved its activity.

EXAMPLE 20

Example 18 was repeated, this time using 16.7 g of methanol instead of 25 g.

Samples were taken after 2 hours, 5 hours and 7 hours. For each sample, after filtering then evaporating off the excess methanol and eliminating the glycerol formed by decanting, the concentration of methyl esters was determined by steric exclusion chromatography. It was 57%, 75% and 92% respectively.

The antimony concentration in the methyl ester obtained was less than 1 ppm, which confirmed the heterogeneous character of the catalysis.

Under the same conditions, the same recycled catalyst produced a methyl ester concentration of 92% after 7 hours of reaction, which indicated that the catalyst had not degraded at all and that it had conserved its activity.

EXAMPLE 21

Example 18 was repeated, this time operating at 180° C. instead of 200° C. The pressure reached 27 bars.

Samples were taken after 2 hours, 5 hours and 7 hours. For each sample, after filtering then evaporating off the excess methanol and eliminating the glycerol formed by decanting, the concentration of methyl esters was determined by steric exclusion chromatography. It was 67%, 82% and 95% respectively.

The antimony concentration in the methyl ester obtained was less than 1 ppm, which confirmed the heterogeneous character of the catalysis.

Under the same conditions, the same recycled catalyst produced a methyl ester concentration of 95% after 7 hours of reaction, which indicated that the catalyst had not degraded at all and that it had conserved its activity.

EXAMPLES 22 TO 24

The procedure of Examples 7 to 9 was carried out, using 70 cm³ of catalyst 3.3.

The table below shows the results obtained after 24 hours of reaction.

In the table:
E=esters (also containing sterols);
MG=monoglycerides;
DG=diglycerides, which contain no sterol esters, as they are not formed under those conditions;
TG=triglycerides.

Methanolysis of Rapeseed Oil with Catalyst 3.3

| Ex. | T (°C.) | HSV | O/A ratio vol./vol. | P (bar) | TG (%) | DG (%) | MG (%) | E (%) | contact time (min) |
|---|---|---|---|---|---|---|---|---|---|
| 22 | 200 | 0.5 | 1 | 50 | 0.4 | 1.1 | 2.9 | 95.6 | 60 |
| 23 | 200 | 0.5 | 1.5 | 50 | 3.6 | 2.8 | 3.8 | 90.3 | 72 |
| 24 | 180 | 0.5 | 1 | 50 | 2.6 | 4.6 | 7.7 | 85.1 | 60 |

Antimony X ray fluorescence analysis was carried out on the methyl esters and the glycerol obtained. The absence of antimony in these products confirmed the heterogeneous nature of the catalyst.

EXAMPLE 25

The procedure of Example 22 was followed, replacing the rapeseed oil used as the feed with an ester mixture the composition of which was identical to that obtained in Example 22.

The composition of the ester phase obtained was:

| Methyl esters: | 99.4% |
|---|---|
| Monoglycerides: | 0.4% |
| Diglycerides: | 0.1% |
| Triglycerides: | not detected |

This composition was compatible with the specifications required for a diesel engine fuel ester.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for producing at least one fatty acid ester and glycerin with a high degree of purity, comprising reacting a vegetable or animal oil with an aliphatic monoalcohol containing 1 to 18 carbon atoms in the presence of at least one catalyst comprising:

mixtures of zirconium oxide and alumina having formula:

$$(ZrO_x)_y(Al_2O_3)_{1-y}$$

where x has the value 1.5 to 2.2 and y has a value of 0.005 to 0.995;

or mixtures of antimony oxide and alumina having formula:

$$(SbO_x)_y(Al_2O_3)_{1-y}$$

where x has the value 1.6 to 2.2 and y has a value of 0.005 to 0.995.

2. A process according to claim 1, wherein said aliphatic monoalcohol contains 1 to 12 carbon atoms.

3. A process according to claim 1, wherein said aliphatic monoalcohol contains 1 to 5 carbon atoms.

4. A process according to claim 1 conducted at temperature of 170° C. to 250° C. at a pressure of less than 100 bars and with an excess of monoalcohol with respect to the oil/alcohol stoichiometry.

5. A process according to claim 1, wherein said catalyst is in the form of a powder, extrudates or beads.

6. A process according to claim 1, wherein the catalyst has a surface area of 10 to 200 m²/g, a pore volume of 0.2 to 1.2 cm³/g and a pore distribution in the range of 0.01 to 0.1 microns.

7. A process according to claim 5, wherein the catalyst has a surface area of 50 to 200 m²/g and a pore volume of more than 0.3 cm³/g.

8. A process according to claim 1, wherein the reaction is carried out discontinuously.

9. A process according to claim 1, wherein the reaction is carried out continuously either in a fixed bed or with autoclaves and decanters in series.

10. A process according to claim 8, wherein the reaction is carried out in a fixed bed, at a HSV of 0.1 to 3.

11. A process according to claim 1, comprising conducting the following steps in succession:
initial transesterification with an oil to ester conversion of at least 80-85%;
evaporating off the excess monoalcohol;
decanting the glycerin and the ester, said ester being recycled to a second step to undergo transesterification with a portion of the monoalcohol recovered in the first evaporation;
then evaporating off the monoalcohol once more, cold decanting and separating the glycerin from the ester.

12. A process according to claim 1, wherein the starting oil is an acidic oil containing free fatty acid and a prior esterification operation is carried out on the free fatty acid, at a temperature in the range of 180° C. to 220° C., and at a pressure of 1 bar or less.

13. A process according to claim 1, wherein the ester obtained is purified, by passage over a resin, an earth and/or activated charcoal.

14. A process according to claim 1, wherein the ester obtained is purified either by distillation or by washing with methanolic glycerin to reduce the monoglyceride content.

15. A process according to claim 9, wherein the HSV is in the range of 0.3 to 2.

16. A process for producing at least one fatty acid ester and glycerin with a high degree of purity, comprising reacting a vegetable or animal oil with an aliphatic monoalcohol containing 1 to 18 carbon atoms in the presence of at least one catalyst comprising:

mixtures of titanium oxide and alumina having formula:

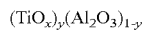

where x has the value 1.5 to 2.2 and y, representing the weight ratio of the two oxides, has a value of 0.005 to 0.995, and wherein the catalyst has a surface area of 10 to 200 m$^2$/g, a pore volume of 0.2 to 1.2 cm$^3$/g and a pore distribution in the range of 0.01 to 0.1 microns, and wherein the reaction is conducted to provide a yield of esters in amount by weight of at least about 90%.

17. A process according to claim 15, wherein the catalyst has a surface area of 50 to 200 m$^2$/g and a pore volume of more than 0.3 cm$^3$/g.

18. A process according to claim 1, wherein said catalyst comprises said mixtures of zirconium oxide and alumina.

19. A process according to claim 1, wherein said catalyst comprises said mixtures of antimony oxide and alumina.

20. A process according to claim 19, wherein the catalyst was prepared by impregnating antimony butoxide into alumina and calcining the resultant mass to achieve a crystalline phase of gamma alumina.

* * * * *

UNITED STATES PATENT AND TRADEMARK OFFICE
CERTIFICATE OF CORRECTION

PATENT NO. : 7,592,470 B2 Page 1 of 1
APPLICATION NO. : 10/853725
DATED : September 22, 2009
INVENTOR(S) : Lacome et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1519 days.

Signed and Sealed this

Twenty-first Day of September, 2010

David J. Kappos
*Director of the United States Patent and Trademark Office*